(12) United States Patent
Beazley et al.

(10) Patent No.: US 8,124,848 B2
(45) Date of Patent: Feb. 28, 2012

(54) GLYPHOSATE TOLERANT ALFALFA EVENTS AND METHODS FOR DETECTION THEREOF

(75) Inventors: Kim A. Beazley, Kirkwood, MO (US); Kenneth L. Ferreira, O'Fallon, MO (US); Sharie N. Fitzpatrick, Onalaska, WI (US); Mark H. McCaslin, Prior Lake, MN (US); Carlos C. Reyes, Meadow Vista, CA (US)

(73) Assignee: Monsanto Technology LLC, St. Louis, MO (US)

( * ) Notice: Subject to any disclaimer, the term of this patent is extended or adjusted under 35 U.S.C. 154(b) by 312 days.

(21) Appl. No.: 12/456,291

(22) Filed: Jun. 15, 2009

(65) Prior Publication Data

US 2009/0282497 A1 Nov. 12, 2009

Related U.S. Application Data

(62) Division of application No. 10/541,834, filed as application No. PCT/US2004/000812 on Jan. 14, 2004, now Pat. No. 7,566,817.

(60) Provisional application No. 60/443,997, filed on Jan. 31, 2003.

(51) Int. Cl.
*A01H 1/00* (2006.01)
*C12N 15/82* (2006.01)

(52) U.S. Cl. ......................... 800/300; 800/266

(58) Field of Classification Search .................. None
See application file for complete search history.

(56) References Cited

U.S. PATENT DOCUMENTS

| 6,057,496 | A | 5/2000 | Conner |
|---|---|---|---|
| 6,462,258 | B1 | 10/2002 | Fincher et al. |
| 2004/0029123 | A1 | 2/2004 | Olek et al. |
| 2004/0048254 | A1 | 3/2004 | Olek et al. |

FOREIGN PATENT DOCUMENTS

| WO | WO 92/04449 A1 | 3/1992 |
|---|---|---|
| WO | WO 99/23232 A1 | 5/1999 |
| WO | WO 01/07632 A1 | 2/2001 |
| WO | WO 01/77384 A2 | 10/2001 |
| WO | WO 02/27004 A2 | 4/2002 |
| WO | WO 02/34946 A2 | 5/2002 |
| WO | WO 02/36831 A2 | 5/2002 |
| WO | WO 02/40677 A2 | 5/2002 |
| WO | WO 02/44407 A2 | 6/2002 |
| WO | WO 2004/070020 A3 | 8/2004 |

OTHER PUBLICATIONS

EMBL Accession No. AL590503, dated Apr. 10, 2001.
McCaslin, "An Update on the Development of Roundup Ready Alfalfa," *Proceedings of the 2002 Western Alfalfa and Forage Conference*, Reno, Nevada, pp. 1-2, 2002.
New England BioLabs Inc. 1998/99 Catalog, (NEB Catalog), pp. 121 and 284, undated.
Final Office Action regarding U.S. Appl. No. 11/801,114, dated Aug. 26, 2009.
GenBank Accession No. AC068821, dated May 10, 2000.
GenBank Accession No. AL133270, dated Jan. 13, 2009.
GenBank Accession No. BG731119, dated May 9, 2001.
Official Action date mailed May 25, 2010 in Australian Patent Application No. 2007237221.
McCaslin, Mark, "An update on the development of Roundup Ready alfalfa," in *Proceedings of the 32nd California Alfalfa and Forage Conference*, Reno, Nevada, Dec. 11-13, 2002, pp. 207-208.
National Advisory Committee on Agricultural Biotechnology [Comisión Nacional Asesora de Biotecnología Agropecuria ("CONABIA")], "2001 Annual Report," *Biotechnología—CONABIA*, Buenos Aires, Jan. 2002, Internet Article Online! [accessed Jun. 22, 2004] (7 pp.).
Cline, Harry, Trials probe Roundup Ready alfalfa, *Western Farm Press* (Oct. 5, 2002), Internet Article Online!.
Comisión Nacional Asesora de Biotecnología Agropecuria [National Advisory Committee on Agricultural Biotechnology ("CONABIA")], "Liberaciones al medio—Permisos otorgados durante el 2002," *Biotechnología—CONABIA*, Buenos Aires, 2002, Internet Article Online! (4 pp.).
Widholm, Jack M., et al., Glyphosate selection of gene amplification in suspension cultures of 3 plant species, *Physiologia Plantarum* 112:540-545 (2001).
McCaslin, Mark, et al.; "Roundup Ready Alfalfa," in *Proceedings of the American Forage and Grassland Council, 37th North American Alfalfa Improvement Conference*, Madison, Wisconsin, Jul. 16-19, 2000, pp. 396-400.

*Primary Examiner* — David H Kruse
(74) *Attorney, Agent, or Firm* — SNR LLP; Pamela Sisson Esq

(57) ABSTRACT

The present invention relates to the field of plant molecular biology and, specifically, to transgenic glyphosate tolerance in an alfalfa plant. The invention more specifically relates to glyphosate tolerant alfalfa events J-101 and J-163 and to assays for detecting the presence of glyphosate tolerant alfalfa DNA in a plant extract.

20 Claims, 7 Drawing Sheets

```
  1  ACATAGCTTT TATGTGAAGG AAAAATCAAA TTTTCCAAAA TTTGGAGTTT
 51  ATAGACTGAG CACATGATAC TGTCGGTGTT TGTTTAAAAG ATTAAAAAAC
101  TATACCCTTT GAATAATTAA ATTAAATCAA ATTTTCATAT TAAATTTTTA
151  ATTTTATAGT AATAATCTAA TTTTAATACA CTTAGGTGTA AAAAAAATTT
201  AAGCTTCAAA GTTTTATATT GTCAGCAAAT CACAACTAAT TGTGTGTACG
251  GATACAAAGT CAAACATGAT TTATTGACGG TGTAAAAAAT CTTTACAGTG
301  ACAATGTATA TGGATTAAAT CGATTTTATA TTAGTTATTT TATGTTATAT
351  CGTATTCATG TCATGTGTTT TGTACTGATC TTGTGTCATA GTTTCAAACA
401  CTGATAGTTT AAACTGAAGG CGGGAAACGA CAATCTGATC CCCATCAAGC
451  TTCTGCAGGT CCTGCTCGAG TGGAAGCTAA TTCTCAGTCC AAAGCCTCAA
501  CAAGGTCAGG GTACAGAGTC TCCAAACCAT TAGCCAAAAG CTACAGGAGA
551  TCAATGAAGA ATCTTCAATC AAAGTAAACT ACTGTTCCAG CACATGCATC
601  ATGGTCAGTA AGTTTCAGAA AAAGACATCC ACCGAAGACT TAAAGTTAGT
651  GGGCATCTTT GAAAGTAATC TTGTCAAC
```

FIGURE 2

| | |
|---|---|
| 1 | GAACTTTCCT TTATGTAATT TTCCAGAATC CTTGTCAGAT TCTAATCATT |
| 51 | GCTTTATAAT TATAGTTATA CTCATGGATT TGTAGTTGAG TATGAAAATA |
| 101 | TTTTTTAATG CATTTTATGA CTTGCCAATT GATTGACAAC ATGCATCAAT |
| 151 | CGACCTGCAG CCACTCGAAG CGGCCGCCAC TCGAGTGGTG GCCGCATCGA |
| 201 | TCGTGAAGTT TCTCATCTAA GCCCCATTT GGACGTGAAT GTAGACACGT |
| 251 | CGAAATAAAG ATTTCCGAAT TAGAATAATT TGTTTATTGC TTTCGCCTAT |
| 301 | AAATACGACG GATCGTATGC ATTAAATATA TAGAGGAATT TCTTATCTTG |
| 351 | CTAATTCCAG CATAGTTATT TTAATTTGTC AAATAATTGT ATGAATGGTA |
| 401 | TATTCTACAA CTTTCTCATG CTTTTCAATA ATGATGTTGT TTTTCTGTAA |
| 451 | TGCTATTTTG ATTTTATTTT GCAGGTGAAC AAGAGCAACA GTGCTTTGAT |
| 501 | CCATATTACA AATGAGGGAT GGTACTATTT TATGGATGCA GTGAAACTTC |
| 551 | TGAAAACATA GTTGGTGTGG TGCTGTTGGA G |

FIGURE 3

```
  1  TTTCTTACTT CCTAGATTTG GTAGGGTTGA AACACATGAA AATTTAAAGC
 51  ATATACACAA TACATTTTGG ACTTGACTTG ACTTCACTAT TCATAATGAG
101  CTTCATGCAT ATTTGGATGC CCATATCATA TCAAGTCATT ATTTTATTTT
151  CCTTTTAACG ATTACCCCCT CCTACTTTTT TCCTTCTTTG CCGGGACAAG
201  GTCATCCAAA CTGAAGTGTT CGGTGGGAAA CGACACTCTG ATCCCCATCA
251  AGCTTCTGCA GGTCCTGCTC GAGTGGAAGC TAATTCTCAG TCCAAAGCCT
301  CAACAAGGTC AGGGTACAGA GTCTCCAAAC CATTAGCCAA AAGCTACAGG
351  AGATCAATGA AGAATCTTCA ATCAAAGTAA ACTACTGTTC CAGCACATGC
401  ATCATGGTCA GTAAGTTTCA GAAAAAGACA TCCACCGAAG ACTTAAAGTT
451  AGTGGGCATC TTTGAAAGTA ATCTTGTCAA C
```

FIGURE 4

```
  1  GAACTTTCCT TTATGTAATT TTCCAGAATC CTTGTCAGAT TCTAATCATT

51  GCTTTATAAT TATAGTTATA CTCATGGATT TGTAGTTGAG TATGAAAATA

101  TTTTTTAATG CATTTTATGA CTTGCCAATT GATTGACAAC ATGCATCAAT

151  CGACCTGCAG CCACTCGAAG CGGCCGCCAC TCGAGTGGTG GCCGCATCGA

201  TCGTGAAGTT TCTCATCTAA GCCCCATTT GGACGTGAAT GTAGACACGT

251  CGAAATAAAG ATTTCCGAAT TAGAATAATT TGTTTATTGC TTTCGCCTAT

301  AAATACGACG GATCGTAATT TGTCGTTTTA TCAAATGTA CTTTCATTTT

351  ATAATAACTT CCATTTTTTT TTTCTTTTTC TTTTATAATA ACAGAAAAAG

401  AAAAAGAAAG ATGATGAAAA GAGAAAAGAG AAAACCGAAC CATGATAATT

451  AACACACCAC GTGCAATTTA CTTTACTTTA ATTTTACTAC TACCTTATTC

501  TTTCTTCAGC GTGGTAACCG TTATACTCTT TATTACACCA CTCACCACCA
```

FIGURE 5

| | | |
|---|---|---|
| A | 5' ACATAGCTTTTATGTGAAGGAAAAATC 3' | (SEQ ID NO:9) |
| E | 5' TTTCTTACTTCCTAGATTTGGTAGG 3' | (SEQ ID NO:10) |
| Z | 5' GTTGACAAGATTACTTTCAAAGATGC 3' | (SEQ ID NO:11) |
| B | 5' CTCCAACAGCACCACACCAACTAT 3' | (SEQ ID NO:12) |
| F | 5' TGGTGGTGAGTGGTGTAATAAAGAG 3' | (SEQ ID NO:13) |
| Y | 5' GAACTTTCCTTTATGTAATTTTCCAG 3' | (SEQ ID NO:14) |

FIGURE 6

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 1
gtcatagttt caaacact                                                    18

<210> SEQ ID NO 2
<211> LENGTH: 18
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 2
cggatcgtat gcattaaa                                                    18

<210> SEQ ID NO 3
<211> LENGTH: 678
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 3
acatagcttt tatgtgaagg aaaaatcaaa tttttccaaaa tttggagttt atagactgag      60
```

```
cacatgatac tgtcggtgtt tgtttaaaag attaaaaaac tatacccttt gaataattaa    120
attaaatcaa attttcatat taaattttta attttatagt aataatctaa ttttaataca    180
cttaggtgta aaaaaattt aagcttcaaa gttttatatt gtcagcaaat cacaactaat    240
tgtgtgtacg gatacaaagt caaacatgat ttattgacgg tgtaaaaaat ctttacagtg    300
acaatgtata tggattaaat cgattttata ttagttattt tatgttatat cgtattcatg    360
tcatgtgttt tgtactgatc ttgtgtcata gtttcaaaca ctgatagttt aaactgaagg    420
cgggaaacga caatctgatc cccatcaagc ttctgcaggt cctgctcgag tggaagctaa    480
ttctcagtcc aaagcctcaa caaggtcagg gtacagagtc tccaaaccat tagccaaaag    540
ctacaggaga tcaatgaaga tcttcaatc aaagtaaact actgttccag cacatgcatc    600
atggtcagta agtttcagaa aaagacatcc accgaagact taaagttagt gggcatcttt    660
gaaagtaatc ttgtcaac                                                 678

<210> SEQ ID NO 4
<211> LENGTH: 581
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 4
gaactttcct ttatgtaatt ttccagaatc cttgtcagat tctaatcatt gctttataat     60
tatagttata ctcatggatt tgtagttgag atgaaaata ttttttaatg catttatga    120 cttgccaatt gattgacaac atgcatcaat cgacctgcag ccactcgaag cggccgccac    180
tcgagtggtg gccgcatcga tcgtgaagtt tctcatctaa gccccatt ggacgtgaat    240 gtagacacgt cgaaataaag atttccgaat tagaataatt tgtttattgc tttcgcctat    300
aaatacgacg gatcgtatgc attaaatata tagaggaatt tcttatcttg ctaattccag    360
catagttatt ttaatttgtc aaataattgt atgaatggta tattctacaa ctttctcatg    420
cttttcaata atgatgttgt ttttctgtaa tgctattttg attttatttt gcaggtgaac    480
aagagcaaca gtgctttgat ccatattaca aatgagggat ggtactattt tatggatgca    540
gtgaaacttc tgaaaacata gttggtgtgg tgctgttgga g                      581

<210> SEQ ID NO 5
<211> LENGTH: 18
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 5
gtgttcggtg ggaaacga                                                  18

<210> SEQ ID NO 6
<211> LENGTH: 18
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 6
tataataact tccatttt                                                  18
```

<210> SEQ ID NO 7
<211> LENGTH: 481
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 7

```
tttcttactt cctagatttg gtagggttga aacacatgaa aatttaaagc atatacacaa      60
tacattttgg acttgacttg acttcactat tcataatgag cttcatgcat atttggatgc     120
ccatatcata tcaagtcatt attttatttt ccttttaacg attacccccct cctactttt     180
tccttctttg ccgggacaag gtcatccaaa ctgaagtgtt cggtgggaaa cgacactctg     240
atccccatca agcttctgca ggtcctgctc gagtggaagc taattctcag tccaaagcct     300
caacaaggtc agggtacaga gtctccaaac cattagccaa aagctacagg agatcaatga     360
agaatcttca atcaaagtaa actactgttc cagcacatgc atcatggtca gtaagtttca     420
gaaaagaca tccaccgaag acttaaagtt agtgggcatc tttgaaagta atcttgtcaa     480
c                                                                     481
```

<210> SEQ ID NO 8
<211> LENGTH: 550
<212> TYPE: DNA
<213> ORGANISM: Artificial Sequence
<220> FEATURE:
<223> OTHER INFORMATION: chimeric DNA of alfalfa genomic DNA and
      transgene insert DNA

<400> SEQUENCE: 8

```
gaactttcct ttatgtaatt ttccagaatc cttgtcagat tctaatcatt gctttataat      60
tatagttata tcatggatt tgtagttgag tatgaaaata tttttaatg cattttatga     120
cttgccaatt gattgacaac atgcatcaat cgacctgcag ccactcgaag cggccgccac     180
tcgagtggtg gccgcatcga tcgtgaagtt tctcatctaa gccccatttt ggacgtgaat     240
gtagacacgt cgaaataaag atttccgaat tagaataatt tgtttattgc tttcgcctat     300
aaatacgacg gatcgtaatt tgtcgttta tcaaaatgta ctttcatttt ataataactt     360
ccattttttt tttcttttc ttttataata acagaaaaag aaaagaaag atgatgaaaa     420
gagaaaagag aaaaccgaac catgataatt aacacaccac gtgcaattta ctttactta     480
attttactac taccttattc ttttcttcagc gtggtaaccg ttatactctt tattacacca     540
ctcaccacca                                                            550
```

<210> SEQ ID NO 9
<211> LENGTH: 27
<212> TYPE: DNA
<213> ORGANISM: Medicago sativa

<400> SEQUENCE: 9

```
acatagcttt tatgtgaagg aaaaatc                                          27
```

<210> SEQ ID NO 10
<211> LENGTH: 25
<212> TYPE: DNA
<213> ORGANISM: Medicago sativa

<400> SEQUENCE: 10

```
tttcttactt cctagatttg gtagg                                            25
```

```
<210> SEQ ID NO 11
<211> LENGTH: 26
<212> TYPE: DNA
<213> ORGANISM: Figwort mosaic virus

<400> SEQUENCE: 11
gttgacaaga ttactttcaa agatgc                                           26

<210> SEQ ID NO 12
<211> LENGTH: 24
<212> TYPE: DNA
<213> ORGANISM: Medicago sativa

<400> SEQUENCE: 12
ctccaacagc accacaccaa ctat                                             24

<210> SEQ ID NO 13
<211> LENGTH: 25
<212> TYPE: DNA
<213> ORGANISM: Medicago sativa

<400> SEQUENCE: 13
tggtggtgag tggtgtaata aagag                                            25

<210> SEQ ID NO 14
<211> LENGTH: 26
<212> TYPE: DNA
<213> ORGANISM: Pisum sativum

<400> SEQUENCE: 14
gaactttcct ttatgtaatt ttccag                                           26
```

GLYPHOSATE TOLERANT ALFALFA EVENTS AND METHODS FOR DETECTION THEREOF

This application is a divisional of U.S. application Ser. No. 10/541,834, filed Jan. 4, 2006 now U.S. Pat. No. 7,566,817, which is a §371 U.S. national phase application of International Application No. PCT/US2004/00812, filed Jan. 14, 2004, and claims benefit of priority to U.S. Provisional Application Ser. No. 60/443,997, filed Jan. 31, 2003, the entire contents of which are incorporated herein by reference.

FIELD OF THE INVENTION

The present invention relates to the field of plant molecular biology, more specifically the invention relates to transgenic glyphosate tolerance in an alfalfa plant. The invention more specifically relates to glyphosate tolerant alfalfa events J-101 and J-163 and to assays for detecting the presence of glyphosate tolerant alfalfa DNA in a plant extract.

BACKGROUND OF THE INVENTION

Alfalfa is an important animal forage crop in many areas of the world. The methods of biotechnology have been applied to alfalfa for improvement of the agronomic traits and the quality of the product. One such agronomic trait important in alfalfa production is herbicide tolerance, in particular, tolerance to glyphosate herbicide.

Alfalfa is a perennial leguminous plant (*Medicago saliva*) of the family Leguminosae (pulse family), the most important pasture and hay plant in North America, also grown extensively in Argentina, S Europe, and Asia. Alfalfa has high yield, high protein content, and prolific growth. However, unlike most grain or fiber crops from which weeds are separated at harvest, weeds are often harvested along with the forage crop, potentially reducing quality. Reductions in quality are often in the form of lower protein content and feed digestibility. Weeds in new alfalfa stands especially reduce yield and crop quality. The major weeds in new alfalfa fields are annuals, such as green foxtail, pigweed, and lambsquarters. Winter annuals, such as flixweed, blue mustard, shepherdspurse, other mustards and downy brome, are more likely to cause serious weed problems in established stands. Perennial weeds, such as foxtail barley and dandelion, are also common weed problems in established alfalfa. Bindweed and Canada thistle are weeds in alfalfa for which there are currently no good control methods. A herbicide tolerant alfalfa event would be a useful trait for managing weeds and maintaining the quality of the forage.

N-phosphonomethylglycine, also known as glyphosate, is a well-known herbicide that has activity on a broad spectrum of plant species. Glyphosate is the active ingredient of Roundup® (Monsanto Co.), a safe herbicide having a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants. Glyphosate tolerance can also be achieved by the expression of EPSPS variants that have lower affinity for glyphosate and therefore retain their catalytic activity in the presence of glyphosate (U.S. Pat. Nos. 5,633,435; 5,094,945; 4,535,060, and 6,040,497). Enzymes that degrade glyphosate in plant tissues (U.S. Pat. No. 5,463,175) are also capable of conferring cellular tolerance to glyphosate. Such genes are used for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (Zhou et al. Plant Cell Rep. 15:159-163, 1995), soybean (WO 9200377) and canola (WO 9204449). The transgenes for glyphosate tolerance and the transgenes for tolerance to other herbicides, e.g. bar gene, Toki et al. Plant Physiol., 100:1503-1507, 1992; Thompson et al. EMBO J. 6:2519-2523, 1987; phosphinothricin acetyltransferase DeBlock et al. EMBO J., 6:2513-2522, 1987, glufosinate herbicide) are also useful as selectable markers or scorable markers and can provide a useful phenotype for selection of plants linked with other agronomically useful traits.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet. 22:421-477, 1988). For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well known polynucleic acid detection method such as the polymerase chain reaction (PCR) or DNA hybridization using polynucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA ("flanking DNA") adjacent to the inserted transgene DNA is known. An event-specific PCR assay is discussed, for example, by Windels et al. (Med. Fac. Landbouww, Univ. Gent 64/5b:459-462, 1999), who identified glyphosate tolerant soybean event 40-3-2 by PCR using a primer set spanning the junction between the insert transgene and flanking DNA, specifically one primer that included sequence from the insert and a second primer that included sequence from flanking DNA. Transgenic plant event specific DNA detection methods have also been described in US 20020013960 and WO 0227004.

This invention relates to the glyphosate herbicide tolerant alfalfa events J-101 and J-163, and to the DNA molecules contained in these alfalfa plants that are useful in detection methods for glyphosate tolerant alfalfa and progeny thereof.

SUMMARY OF THE INVENTION

The present invention is an alfalfa transgenic event designated J-101 having seed deposited with American Type Culture Collection (ATCC) with Accession No. PTA-4814. Another aspect of the invention is the progeny plants, or seeds, or regenerable parts of the plants and seeds of the alfalfa event J-101. The invention also includes plant parts of alfalfa event J-101 that include, but are not limited to pollen, ovule, flowers, shoots, roots, and leaves. The invention provides a glyphosate tolerant alfalfa plant that has all of the physiological and morphological characteristics of the alfalfa event J-101 of claim 1 and the progeny plants and parts thereof.

One aspect of the invention provides compositions and methods for detecting the presence of a DNA transgene/genomic junction region from alfalfa event J-101 plant or seed. DNA molecules are provided that comprise at least one transgene/genomic junction DNA molecule selected from the group consisting of SEQ ID NO:1 and SEQ ID NO:2, and complements thereof, wherein the junction molecule spans the insertion site that comprises a heterologous DNA inserted into the genome and the genomic DNA from the alfalfa cell flanking the insertion site alfalfa event J-101. An alfalfa event J-101 and seed comprising these DNA molecules is an aspect of this invention.

A novel DNA molecule is provided that is a DNA transgene/genomic region SEQ ID NO:3 or the complement thereof, from alfalfa event J-101. An alfalfa plant and seed comprising SEQ ID NO:3 in its genome is an aspect of this invention. According to another aspect of the invention, a DNA molecule is provided that is a DNA transgene/genomic region SEQ ID NO:4, or the complement thereof, wherein this DNA molecule is novel in alfalfa event J-101. An alfalfa plant and seed comprising SEQ ID NO:4 in its genome is an aspect of this invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:3 and a DNA molecule of similar length of any portion of a 5' flanking alfalfa genomic DNA region of SEQ ID NO:3, where these DNA molecules when used together are useful as DNA primers in a DNA amplification method that produces an amplicon. The amplicon produced using these DNA primers in the DNA amplification method comprises SEQ ID NO:1 and is diagnostic for alfalfa event J-101. Any amplicon produced by DNA primers homologous or complementary to any portion of SEQ ID NO:3 that further comprises SEQ ID NO:1 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:4 and a DNA molecule of similar length of any portion of a 3' flanking alfalfa genomic DNA of SEQ ID NO:4, wherein these DNA molecules are useful as DNA primers in a DNA amplification method. The amplicon produced using these DNA primers in the DNA amplification method comprises SEQ ID NO:2 and is diagnostic for alfalfa event J-101. Any amplicon produced by DNA primers homologous or complementary to any portion of SEQ ID NO:4 that further comprises SEQ ID NO:2 is an aspect of the invention.

The invention further includes the alfalfa plant or seed, the genome DNA of which contains SEQ ID NO:3 or SEQ ID NO:4 or an amplicon is produced in a DNA amplification methods that comprises SEQ ID NO:1 or SEQ ID NO:2

According to another aspect of the invention, methods of detecting the presence of DNA corresponding specifically to the alfalfa event J-101 DNA in a sample are provided. Such methods comprise: (a) contacting the sample comprising DNA with a primer set that, when used in a nucleic acid amplification reaction with genomic DNA from alfalfa event J-101 produces a DNA amplicon comprising SEQ ID NO:1 or SEQ ID NO:2 that is diagnostic for alfalfa event J-101 (b) performing a nucleic acid amplification reaction, thereby producing the amplicon; and (c) detecting the amplicon.

According to another aspect of the invention, methods of detecting the presence of DNA corresponding specifically to the alfalfa event J-101 DNA in a sample are provided. Such methods comprising: (a) contacting the sample comprising DNA with a probe comprising SEQ ID NO:1 or SEQ ID NO:2 that hybridizes under stringent hybridization conditions with genomic DNA from alfalfa event J-101 and does not hybridize under the stringent hybridization conditions with a control alfalfa plant DNA; (b) subjecting the sample and probe to stringent hybridization conditions; and (c) detecting hybridization of the probe to the alfalfa event J-101 DNA.

According to another aspect of the invention, methods of producing an alfalfa plant that tolerates application of glyphosate are provided that comprise the steps of: (a) sexually crossing a first parental glyphosate tolerant alfalfa event J-101, and a second parental alfalfa plant that lacks the glyphosate tolerance, thereby producing a plurality of progeny plants; and (b) selecting a progeny plant that tolerates application of glyphosate. Breeding methods may comprise the steps of crossing the parental alfalfa event J-101 plant to a second parental alfalfa plant that is also tolerant to glyphosate and selecting for glyphosate tolerant progeny by molecular marker DNA genetically linked to the glyphosate tolerant phenotype found in each parent.

The present invention further relates to an alfalfa transgenic event designated J-163 having seed deposited with American Type Culture Collection (ATCC) with Accession No. PTA-4815. Another aspect of the invention is the progeny plants, or seeds, or regenerable parts of the plants and seeds of the alfalfa event J-163. The invention also includes plant parts of alfalfa event J-163 that include, but are not limited to pollen, ovule, flowers, shoots, roots, and leaves.

The invention provides a glyphosate tolerant alfalfa plant that has all of the physiological and morphological characteristics of the alfalfa event J-163 of claim 1 and the progeny plants and parts thereof.

One aspect of the invention provides compositions and methods for detecting the presence of a transgene/genomic junction region from alfalfa event J-163. DNA molecules are provided that comprise at least one transgene/genomic junction DNA molecule selected from the group consisting of SEQ ID NO:5 and SEQ ID NO:6, and complements thereof, wherein the junction molecule spans the insertion site that comprises a heterologous DNA inserted into the genome and the genomic DNA from the alfalfa cell flanking the insertion site alfalfa event J-163. An alfalfa event J-163 and seed comprising these DNA molecules is an aspect of this invention.

A novel DNA molecule is provided that is a transgene/ genomic region SEQ ID NO:7 or the complement thereof, wherein this DNA molecule is novel in alfalfa event J-163. An alfalfa plant and seed comprising SEQ ID NO:7 in its genome is an aspect of this invention. According to another aspect of the invention, a DNA molecule is provided that is a transgene/ genomic region SEQ ID NO: 8, or the complement thereof, wherein this DNA molecule is novel in alfalfa event J-163. An alfalfa plant and seed comprising SEQ ID NO:8 in its genome is an aspect of this invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:7 and a DNA molecule of similar length of any portion of a 5' flanking alfalfa genomic DNA region of SEQ ID NO:7, where these DNA molecules when used together are useful as DNA primers in a DNA amplification method that produces an amplicon that comprises SEQ ID NO:5. The amplicon produced using these DNA primers in the DNA amplification method is diagnostic for alfalfa event J-163. Any amplicon comprising SEQ ID NO:5 produced by DNA primers homologous or complementary to any portion of SEQ ID NO:7 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:8 and a DNA molecule of similar length of any portion of a 3' flanking alfalfa genomic DNA of SEQ ID NO:8, where these DNA molecules are useful as DNA primers in a DNA amplification method. The amplicon comprising SEQ ID NO:6 produced using these DNA primers in the DNA amplification method is diagnostic for alfalfa event J-163. The amplicon comprising SEQ ID NO:6 produced by DNA primers homologous or complementary to any portion of SEQ ID NO:8 are an aspect of the invention.

An alfalfa plant or seed, the genomic DNA that when isolated from the alfalfa plant or seed produces an amplicon diagnostic for alfalfa event J-163 when tested in a DNA amplification method is an aspect of the invention.

According to another aspect of the invention, methods of detecting the presence of DNA corresponding specifically to the alfalfa event J-163 DNA in a sample are provided. Such methods comprise: (a) contacting the sample comprising DNA with a primer set that, when used in a nucleic acid amplification reaction with genomic DNA from alfalfa event J-163 produces an amplicon comprising SEQ ID NO:5 or SEQ ID NO:6 that is diagnostic for alfalfa event J-163 (b) performing a nucleic acid amplification reaction, thereby producing the amplicon; and (c) detecting the amplicon.

According to another aspect of the invention, methods of detecting the presence of DNA corresponding specifically to the alfalfa event J-163 DNA in a sample are provided. Such methods comprising: (a) contacting the sample comprising DNA with a probe comprising SEQ ID NO:5 or SEQ ID NO:6 that hybridizes under stringent hybridization conditions with genomic DNA from alfalfa event J-163 and does not hybridize under the stringent hybridization conditions with a control alfalfa plant DNA; (b) subjecting the sample and probe to stringent hybridization conditions; and (c) detecting hybridization of the probe to the alfalfa event J-163 DNA.

According to another aspect of the invention, methods of producing an alfalfa plant that tolerates application of glyphosate are provided that comprise the steps of: (a) sexually crossing a first parental glyphosate tolerant alfalfa event J-163, and a second parental alfalfa plant that lacks the glyphosate tolerance, thereby producing a plurality of progeny plants; and (b) selecting a progeny plant that tolerates application of glyphosate. Breeding methods may comprise the steps of crossing the parental alfalfa event J-163 plant to a second parental alfalfa plant that is also tolerant to glyphosate and selecting for glyphosate tolerant progeny by molecular marker DNA genetically linked to the glyphosate tolerant phenotype found in each parent.

According to a further aspect of the invention there is provided an alfalfa plant or seed, wherein its genome will produce an amplicon comprising SEQ ID NO:1, or 2, and 5 or 6 diagnostic for alfalfa event J-101 and alfalfa event J-163 when tested in a DNA amplification method to amplify a DNA molecule from the alfalfa plant or seed. The alfalfa plant or seed also comprises in its genome a DNA molecule selected from the group consisting of SEQ ID NO:1-8.

Another aspect of the invention is a mixture of alfalfa seed, the mixture comprising alfalfa event J-101 seed and alfalfa event J-163 seed. A field of alfalfa plants comprising the mixture of alfalfa plants J-101 and J-163 is an aspect of the invention.

The invention provides for glyphosate tolerant alfalfa plants that when grown in a field and treated with a herbicide formulation containing glyphosate provide an essentially weed-free alfalfa hay crop.

The foregoing and other aspects of the invention will become more apparent from the following detailed description and accompanying drawings.

BRIEF DESCRIPTION OF THE DRAWINGS

FIG. 2. 5' transgene/genome DNA sequence isolated from J-101.

FIG. 3. 3' transgene/genome DNA sequence isolated from J-101.

FIG. 4. 5' transgene/genome DNA sequence isolated from J-163.

FIG. 5. 3' transgene/genome DNA sequence isolated from J-163.

FIG. 6. DNA primers used to produce an amplicon from Alfalfa event J-101 or J-163.

DETAILED DESCRIPTION OF THE PREFERRED EMBODIMENTS

Figure 1:
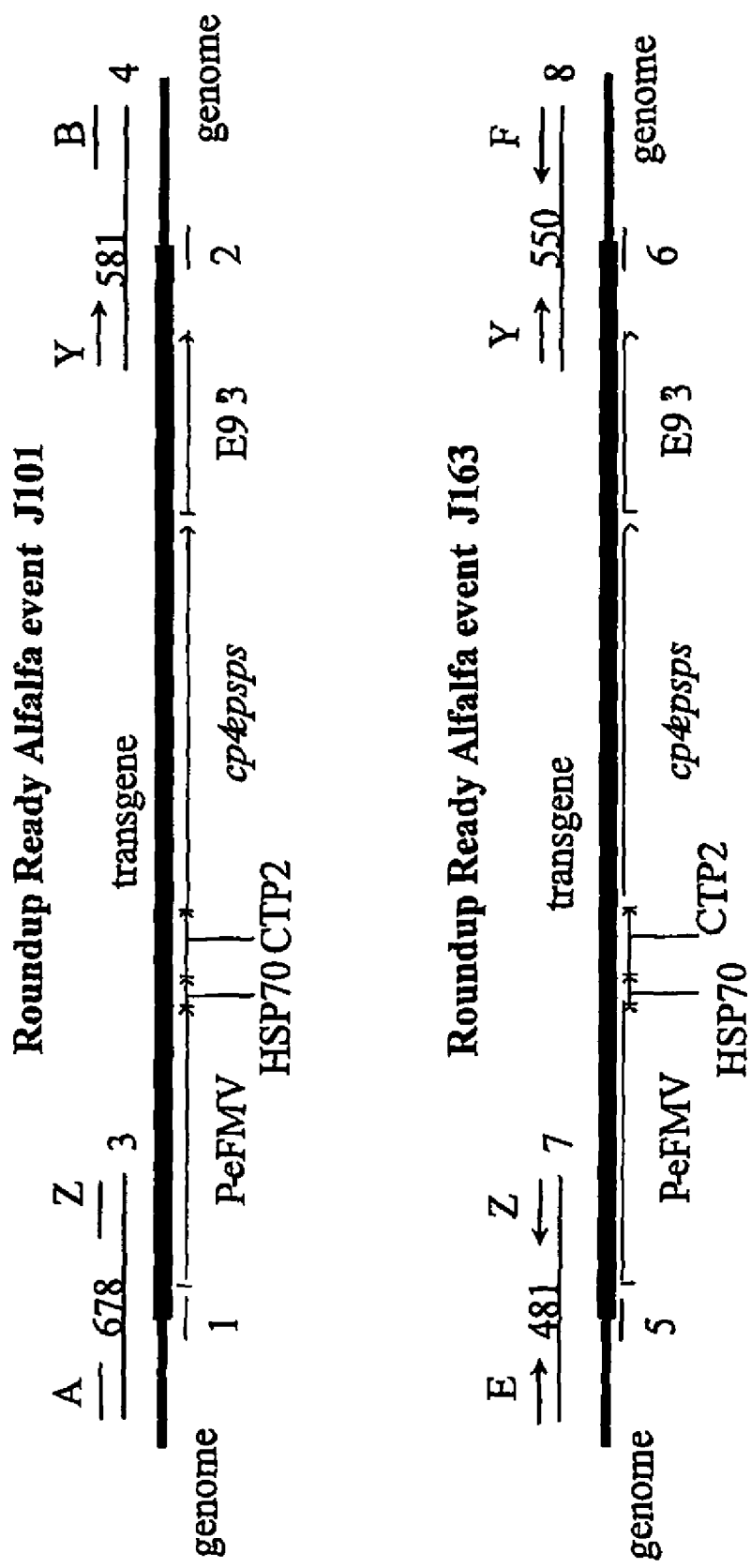
FIG. 1. Organization of the transgene inserts in the genomes of Alfalfa events J-101 and J-163, and location of DNA primers and amplicons.

The invention relates to glyphosate tolerant alfalfa. In particular to two alfalfa events, J-101 and J-163 that can be used singly, as a seed mixture, or as progeny from a breeding cross of the two events to provide a field of alfalfa that can be treated with glyphosate containing herbicide formulations to provide an essentially weed-free alfalfa hay crop. The invention further relates to DNA molecules that can be used to specifically identify J-101 and J-163 DNA in a sample containing alfalfa DNA. The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical*

*and Molecular*, 5th edition, Springer-Verlag: New York, 1991; and Lewin, *Genes V*, Oxford University Press: New York, 1994. The nomenclature for DNA bases as set forth at 37 CFR §1.822 is used.

As used herein, the term "alfalfa" means *Medicago sativa* and includes all plant varieties that can be bred with alfalfa. Alfalfa is also called medic, the name for any plant of the genus *Medicago* Old World herbs with blue or yellow flowers similar to those of the related clovers. Black medic (*M. lupulina*) and the bur clovers (*M. arabica* and *M. hispida*) are among the annual species naturalized in North America and sometimes also grown for bay and pasture. Alfalfa is classified in the division Magnoliophyta, class Magnoliopsida, order Rosales, family Leguminosae. Unlike corn or soybeans, alfalfa plants are autotetraploid; that is, each trait is determined by genes residing in four chromosomes instead of two. That makes genetics research very complex and adds to the difficulty of improving alfalfa. Commercial alfalfa seed is often comprised of a mixture of clones that may constitute a synthetic cultivar generated by random interpollination among the selected clones, followed by one to three generations of open-pollination in isolation. A composite cultivar of alfalfa may also be developed by blending seed of two or more clones or by interpollinating clones in isolation. In forming a composite cultivar, equal quantities of seed from each component clone would be blended to form the initial breeder seed stock. Methods for breeding transgenic alfalfa plants have been described in U.S. Patent Application No. 20020042928 (herein incorporated by reference in its entirety).

As used herein, the term "comprising" means "including but not limited to".

"Glyphosate" refers to N-phosphonomethylglycine and its salts, Glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation containing glyphosate. Examples of commercial formulations of glyphosate include, without restriction, those sold by Monsanto Company as ROUNDUP®, ROUNDUP® ULTRA, ROUNDUP® ULTRAX, ROUNDUP® WEATHERMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Syngenta Crop Protection as TOUCHDOWN® herbicide, which contains glyphosate as its trimethylsulfonium salt A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous transgene DNA. Even after repeated back-crossing to a recurrent parent, the inserted transgene DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The glyphosate tolerant events of the present invention are referred to herein as J-101 and J-163. The present invention provides for the seeds and plant parts of J-101 and J-163 and for the seeds and plant parts of synthetic cultivars produced by the combination of the genomes of both.

A glyphosate tolerant alfalfa plant can be breed by first sexually crossing a first parental alfalfa plant consisting of an alfalfa plant grown from the transgenic alfalfa plant J-101 or J-163 or an alfalfa plant that is a progeny of the cross of J-101 and J-163 that expresses the glyphosate tolerant phenotype, and a second parental alfalfa plant that lacks the tolerance to glyphosate herbicide, thereby producing a plurality of first progeny plants; and then selecting a progeny plant that is tolerant to application of glyphosate herbicide. These steps can further include the back-crossing of the glyphosate tolerant progeny plant to the second parental alfalfa plant or a third parental alfalfa plant, then selecting progeny by application with glyphosate or by identification with molecular markers associated with the trait thereby producing an alfalfa plant that tolerates the application of glyphosate herbicide. Molecular markers comprise the junction sequences identified at the 5' and 3' sites of insertion of the transgene in alfalfa J-101 and J-163.

Applications of herbicide formulations that contain glyphosate can be applied to a field of alfalfa plants that comprise J-101 or J-163, or a mixture of the seed of each, or a synthetic cultivar that contains the genomic portions of J-101 and J-163 that contain the transgene of the present invention. The rates of glyphosate treatments to the field can be up to about 6 pounds of acid equivalent (lb ae)/year divided into multiple applications where no one treatment exceeds about 1.5 lb ae glyphosate. These rates provide a high level of weed control in the field of alfalfa. The hay crop cut from the alfalfa field is of high quality and essentially weed free.

It is also to be understood that two different transgenic plants can also be mated to produce offspring that contain two independently segregating, exogenous transgenes. Back-crossing to a parental plant and out-crossing with a non-transgenic plant as previously described is also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987). Specifically for alfalfa breeding, the methods described in U.S. Patent Application No. 20020042928 are particularly useful for breeding transgenic alfalfa events. The resulting alfalfa plant and seed comprise a mixture of the genotypes of transgenic alfalfa events. The genotypes result from crosses of dihomogenics (AxxxByyy, where A and B are the transgenes) that are obtained from crossing (Axxxyyyy)×(xxxxByyy) and the dihomogenic progeny are identified by PCR. Intercrossing of the dihomogenics results in the synthetic alfalfa cultivar that is the commercial product. In the present invention, a commercial alfalfa product can contain genomic mixture that comprises J-101 and J-163 transgene/genome DNA.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from alfalfa event whether from an alfalfa plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated polynucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 polynucleotides or more in length, preferably 18 polynucleotides or more, more preferably 24 polynucleotides or 30 polynucleotides or more. Such probes and primers hybridize specifically to a target sequence under high stringency hybridization conditions. Preferably, probes and primers according to the present invention have complete sequence identity with the target sequence, although probes differing from the target sequence and that retain the ability to hybridize to target sequences under high stringency conditions may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications,* Academic Press: San Diego, 1990. PCR-primer pairs (a primer set) can be derived from a known sequence, for example, by using computer programs intended for that purpose such as Primer (Version 0.5, © 1991, Whitehead Institute for Biomedical Research, Cambridge, Mass.).

Primers and probes based on the flanking genomic DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure and are of sufficient length to maintain this structure under high stringency conditions. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach,* IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology,* John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO:1-8, complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1-8, complements thereof or fragments of either under high stringency conditions. In one aspect of the present invention, a preferred marker nucleic acid molecule of the present invention comprises the nucleic acid sequence as set forth in SEQ ID NO:1 or SEQ ID NO:2 or SEQ ID NO: 5 or SEQ ID NO:6 complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:1 or SEQ ID NO:2 or SEQ ID NO: 5 or SEQ ID NO:6 complements thereof or fragments of either. Molecular marker DNA molecules that comprise SEQ ID NO:1, or SEQ ID NO:2, or SEQ ID NO: 5 or SEQ ID NO:6 complements thereof or fragments of either may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether the alfalfa plant resulting from a sexual cross contains transgenic event J-101 or J-163 or both genomic DNA, DNA extracted from a alfalfa plant tissue sample may be subjected to a nucleic acid amplification method using a primer pair that includes a primer derived from the genomic region adjacent to the insertion site of inserted heterologous transgene DNA, and a second primer derived from the inserted heterologous transgene DNA to produce an amplicon that is diagnostic for the presence of the event DNA. The amplicon is of a length and has a sequence that is also diagnostic for the event. The amplicon may range in length from the combined length of the primer pairs plus one nucleotide base pair, or plus about fifty nucleotide base pairs, or plus about two hundred-fifty nucleotide base pairs, or plus about three hundred-fifty nucleotide base pairs or more. Alternatively, a primer pair can be derived from flanking genomic sequence on both sides of the inserted DNA so as to produce an amplicon that includes the entire insert nucleotide sequence. A member of a primer pair derived from the plant genomic sequence may be located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification reaction methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from alfalfa event J-101 and J-163 can be verified (and corrected if necessary) by amplifying such sequences from the event genome using primers derived from the sequences provided herein and genomic DNA extracted from the representative samples deposited with the ATCC as PTA-4814 and PTA-4815, followed by standard DNA sequencing methods applied to the PCR amplicon or to isolated cloned transgene/genomic DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA transgene sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal, which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking genomic/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

DNA detection kits can be developed using the compositions disclosed herein and the methods well known in the art of DNA detection. The kits are useful for the identification of alfalfa event DNA in a sample and can be applied to methods for breeding alfalfa plants containing DNA. The kits may contain DNA primers or probes that are homologous or complementary to SEQ ID NO:1-8 or DNA primers or probes homologous or complementary to DNA contained in the transgene genetic elements of DNA, these DNA sequences can be used in DNA amplification reactions or as probes in a DNA hybridization method. The sequences of the transgene genetic elements contained in the alfalfa genome (FIG. 1) consists a fragment of the right border region from *Agrobacterium tumefaciens*, the Figwort mosaic promoter (U.S. Pat. No. 6,018,100, herein incorporated by reference in its entirety), wherein the promoter has been duplicated (herein referred to as P-eFMV or P-FMV35Sen) and is operably connected to a *Petunia hybrida* Hsp70 leader (herein referred to as HSP70 or L-Ph.Hsp70, U.S. Pat. No. 5,659,122, herein incorporated by reference in its entirety) and an *Arabidopsis* EPSPS chloroplast transit peptide coding sequence (herein referred to as CTP2 or TS-AtEPSPS CTP2, U.S. Pat. No. 5,633,435, herein incorporated by reference in its entirety), operably connected to a glyphosate resistant EPSPS (herein referred to as CP4 EPSPS or aroA:CP4, isolated from *Agrobacterium tumefaciens* strain CP4, U.S. Pat. No. 5,633,435), operably connected to the 3' termination region from pea ribulose 1,5-bisphosphate carboxylase (herein referred to as E9 3' or T-Ps.RbcS:E9, Coruzzi, et al., EMBO J. 3:1671-1679, 1984), and the left border (LB) region from *Agrobacterium tumefaciens*. DNA molecules useful as primers in DNA amplification methods can be derived from the sequences of the genetic elements of the transgene insert contained in alfalfa event. These primer molecules can be used as part of a primer set that also includes a DNA primer molecule derived from the genome of event flanking the transgene insert.

Figure 7:
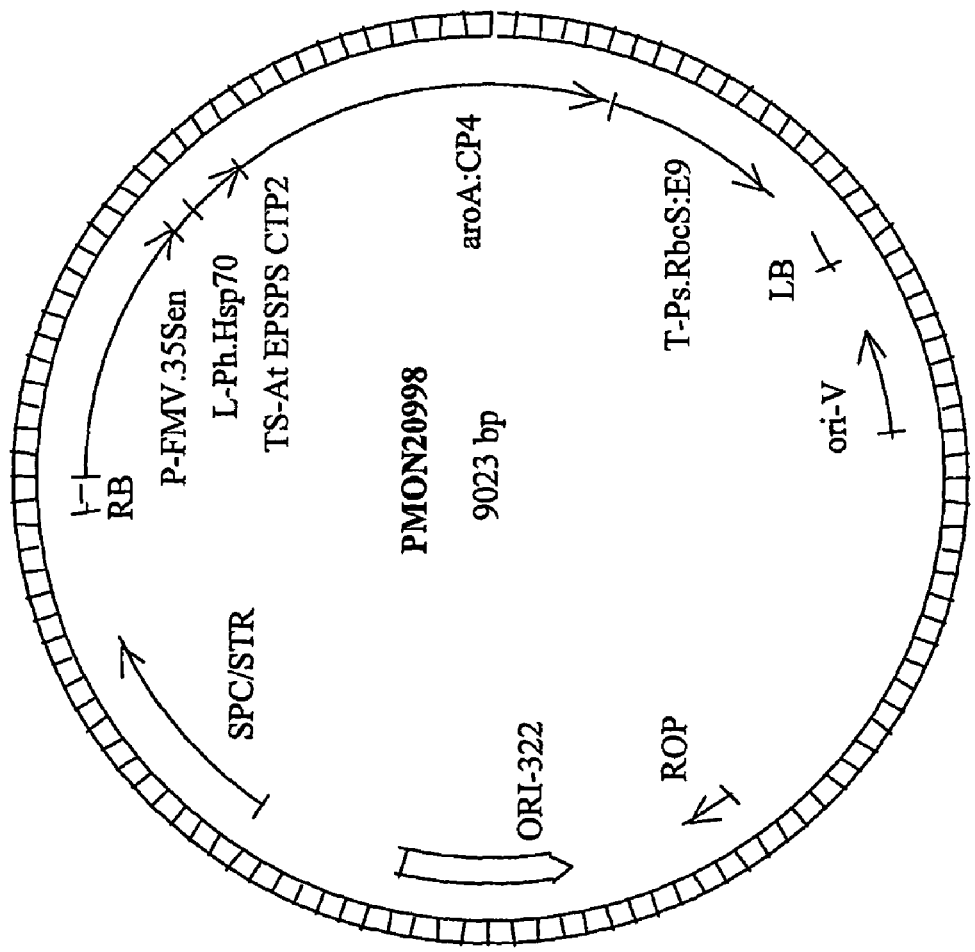
FIG. 7. Plasmid map of pMON20998 used to produce glyphosate tolerant alfalfa plants.

Alfalfa events J-101 and J-163 were produced by transformation of Alfalfa line R2336 by modification of an *Agrobacterium* mediated method (Walker et al., Plant Cell, Tissue and Organ Culture 1:109-121, 1981). Briefly, sterile alfalfa leaf pieces (2-3 mm) are mixed with a suspension of *Agrobacterium* (containing pMON20998, FIG. 7) with 0.05% silwet L-77 (Setre Chemical Co., Memphis, Tenn.). The pieces are blotted onto sterile filter paper, then placed onto sterile filter paper resting on a spread of alfalfa suspension cells, then co-cultivate for 3 days. Following co-cultivation, the explants are transferred to SHDN media containing 500 mg/L ticarcillin (Gujisawa Chemicals, Minn.), after 3 days, the explants are transferred to SHDN media containing 5 mM glyphosate, 500 mg/L ticarcillin, the explants are transferred to fresh media every 2-3 weeks for 8-9 weeks. Shoots are rooted and transferred to soil.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

DNA from transgenic alfalfa event J-101 or J-163 was extracted from alfalfa seeds. The DNA was isolated from the seed tissue using Qiagen's DNeasy Plant Miniprep Kit according to the manufacturer's instructions (Qiagen Corp. Valencia, Calif.). PCR of the genomic DNA sequences flanking the 5' end of the T-DNA insertion in events J-101 or J-163 was performed using one primer designed to the genomic DNA sequences flanking the 5' end of the transgene insert of each event (DNA primers A (SEQ ID NO:9), and E (SEQ ID NO:10), FIG. 1) paired with a second primer (DNA primer Z (SEQ ID NO:11), FIG. 1) located at the 5' end of the insert in the duplicated FMV35S promoter (P-FMV35Sen, tandem duplication of the promoter from the Figwort mosaic virus, U.S. Pat. No. 6,018,100). PCR analysis of the genomic DNA sequences flanking the 3' end of the T-DNA insertion in events J-101 or J-163 was performed using one primer designed to the genomic DNA sequences flanking the 3' end of the insert of each event (DNA primers B (SEQ ID NO:12) and F (SEQ ID NO:13), FIG. 1) paired with a DNA primer Y (SEQ ID NO:14, FIG. 1) located in the E9 3' transcription termination sequence at the 3' end of the insert. The DNA sequences of these primer molecules are shown in FIG. 6. The PCR analyses were performed using ~50 nanogram (ng) of events J-101 and J-163 genomic DNA and ~50 ng of genomic DNA template from the non-transgenic alfalfa cultivar R2336 as a negative control. Each PCR reaction contained, 5 μl 10× Buffer for REDAccuTaq™ LA DNA Polymerase Mix (Sigma-Aldrich, St Louis, Mo.), 200 μM each dNTP (Sigma-Aldrich), 0.4 μM each primer, and 2.5 Units JumpStart™ REDTaq™ DNA Polymerase (Sigma-Aldrich) in a 50 μl total volume reaction. The PCR reactions were performed under the following cycling conditions: 1 cycle at 94° C. for 3 min; 32 or 35 cycles at 94° C. for 30 s, 58° C. for 30 s, 72° C. for 30 s or 1 min; 1 cycle at 72° C. for 10 min.

DNA event primer pairs are used to produce an amplicon diagnostic for J-101 or J-163 genomic DNA. These event primer pairs include, but are not limited to primers A and Z, and Y and B for J-101, and primer E and Z, and Y and F for J-163 that are used in the described DNA amplification method. In addition to these primer pairs, any primer pair derived from SEQ ID NO:3 or SEQ ID NO:4, or SEQ ID NO:7 or SEQ ID NO:8, or the complements thereof, that when used in a DNA amplification reaction produces an amplicon diagnostic for alfalfa J-101 or J-163 events, respectively, is an aspect of the present invention. DNA amplification conditions illustrated in Table 1 and Table 2 can be used to produce a diagnostic amplicon from J-101 or J-163 using the appropriate event primer pairs. A diagnostic amplicon comprises SEQ ID NO:1 or SEQ ID NO:2 for J-101, and SEQ ID NO:5 or SEQ ID NO:6 for J-163. Any modification of these methods used to produce an amplicon diagnostic for J-101 or J-163 event is within the ordinary skill of the art. An alfalfa plant or seed, the genome of which produces an amplicon diagnostic for alfalfa event J-101 or J-163 when tested in a DNA amplification method is an aspect of the present invention.

The amplicon produced by the use of at least one primer sequence derived from SEQ ID NO:3 or SEQ ID NO:4 for J-101, or at least one primer sequence derived from SEQ ID NO:7 or SEQ ID NO:8 for J-163, that when used in a PCR method produces a diagnostic amplicon comprising SEQ ID NO:1, or 2, or 5 or 6 is an aspect of the invention. The production of the J-101 or J-163 amplicons can be performed using a Stratagene Robocycler, MJ Engine, Perkin-Elmer 9700, or Eppendorf Mastercycler Gradient thermocycler as shown in Table 2, or by methods and apparatus known to those skilled in the art.

TABLE 1

PCR procedure and reaction mixture conditions for the identification of alfalfa J-101 5' transgene insert/genomic junction region.

| Step | Reagent | Amount | Comments |
|---|---|---|---|
| 1 | Nuclease-free water | add to final volume of 20 µl | — |
| 2 | 10X reaction buffer (with MgCl$_2$) | 2.0 µl | 1X final concentration of buffer, 1.5 mM final concentration of MgCl$_2$ |
| 3 | 10 mM solution of dATP, dCTP, dGTP, and dTTP | 0.4 µl | 200 µM final concentration of each dNTP |
| 4 | Event primer A (SEQ ID NO: 9 resuspended in 1X TE buffer or nuclease-free water to a concentration of 10 µM) | 0.2 µl | 0.1 µM final concentration |
| 5 | Event primer Z (SEQ ID NO: 11 resuspended in 1X TE buffer or nuclease-free water to a concentration of 10 µM) | 0.2 µl | 0.1 µM final concentration |
| 6 | RNase, DNase free (500 µg/ml) | 0.1 µl | 50 ng/reaction |
| 7 | REDTaq DNA polymerase (1 unit/µl) | 1.0 µl (recommended to switch pipets prior to next step) | 1 unit/reaction |
| 8 | Extracted DNA (template): Samples to be analyzed: individual leaves pooled leaves (maximum of 10 leaves/pool) Negative control Negative control Positive control | 10-200 ng of genomic DNA 200 ng of genomic DNA 50 ng of non-transgenic alfalfa genomic DNA no template DNA (solution in which DNA was resuspended) 50 ng of alfalfa J-101 genomic DNA | — |

Gently mix and, if needed (no hot top on thermocycler), add 1-2 drops of mineral oil on top of each reaction. Proceed with the PCR in a Stratagene Robocycler, MJ Engine, Perkin-Elmer 9700, or Eppendorf Mastercycler Gradient thermocycler using the following cycling parameters (Table 2). The MJ Engine or Eppendorf Mastercycler Gradient thermocycler should be run in the calculated mode. Run the Perkin-Elmer 9700 thermocycler with the tamp speed set at maximum.

TABLE 2

Thermocycler conditions

| Cycle No. | Settings: Stratagene Robocycler |
|---|---|
| 1 | 94° C. 3 minutes |
| 34 | 94° C. 1 minute 64° C. 1 minute 72° C. 1 minute and 30 seconds |
| 1 | 72° C. 10 minutes |

| Cycle No. | Settings: MJ Engine or Perkin-Elmer 9700 |
|---|---|
| 1 | 94° C. 3 minutes |
| 34 | 94° C. 30 seconds 64° C. 30 seconds 72° C. 1 minute |
| 1 | 72° C. 10 minutes |

| Cycle No. | Settings: Eppendorf Mastercycler Gradient |
|---|---|
| 1 | 94° C. 3 minutes |
| 34 | 94° C. 15 seconds 64° C. 15 seconds 72° C. 1 minute |
| 1 | 72° C. 10 minutes |

Example 2

DNA sequencing of the PCR products provides for DNA that can be used to design additional DNA molecules as primers and probes for the identification of alfalfa J-101 or J-163. PCR products of the expected sizes representing the 5' and 3' transgene/genomic sequences were isolated by separation of the PCR products on a 2.0% agarose gel by electrophoresis. PCR products were isolated that are the 5' and 3' DNA regions that span the insert junction between the transgene insertion into the alfalfa genome. The 5' and 3' PCR products for events J-101 and J-163 were purified by agarose gel electrophoresis followed by isolation from the agarose matrix using the QIAquick Gel Extraction Kit (catalog #28704, Qiagen Inc., Valencia, Calif.). The purified PCR products were then sequenced with by DNA sequence analysis (ABI Prism™ 377, PE Biosystems, Foster City, Calif. and DNASTAR sequence analysis software, DNASTAR Inc., Madison, Wis.).

The DNA sequence was determined for a 678 nucleotide base pair segment (FIG. 2) representing the 5' transgene/genomic sequence of alfalfa J-101 (FIG. 1) event and identified in SEQ ID NO:3. The DNA primers are indicated on FIG. 1 as well as the SEQ ID Nos. The DNA sequence was determined for a 581 nucleotide base pair segment (FIG. 3) representing the 3' transgene/genomic sequence of alfalfa J-101 (FIG. 1) event and identified in SEQ ID NO:4. The sequence data shown in FIG. 2 consists of the 5' amplicon encompassing 393 bases of alfalfa genomic DNA (underlined), and 285 bases of the transgene insert containing 2 bp of right border region, 83 bases of polylinker, and 200 bases of P-FMV35Sen promoter. The sequence data shown in FIG. 3 consists of the 3' amplicon encompassing 140 bases of the E9 3' polyadenylation signal sequence and 177 bases of polylinker from the transgene insert, as well as 264 bases representing the alfalfa genomic DNA sequence (underlined) flanking the 3' end of the transgene insert in event J101.

The DNA sequence was determined for a 481 nucleotide base pair segment (FIG. 4) representing the 5' transgene/ genomic sequence of alfalfa J-163 event and identified in SEQ ID NO:7. The DNA sequence was determined for a 550 nucleotide base pair segment (FIG. 5) representing the 3' transgene/genomic sequence of alfalfa J-101 event and identified in SEQ ID NO:8. The sequence data shown in FIG. 4 consists of the 5' amplicon encompassing 224 bases of alfalfa genomic DNA flanking sequence (underlined), and 257 bases of the transgene insert containing 57 bases of polylinker and 200 bases of the P-FMV35Sen promoter. The sequence data shown in FIG. 5 consists of the 3' amplicon encompassing 140 bases of the E9 3' transcription termination sequence, 218 bases of DNA transgene construct sequence and 192 bases of the alfalfa genomic DNA sequence (underlined) flanking the 3' end of the DNA transgene insert in event J163.

The junction sequences are relatively short polynucleotide molecules that are novel DNA sequences and are diagnostic for alfalfa event J-101 and J-163 and progeny thereof. The junction sequences in SEQ ID NO:1 and SEQ ID NO:2 represent 9 polynucleotides on each side of an insertion site of the transgene sequence fragment and alfalfa genomic DNA in J-101, longer or shorter polynucleotide junction sequences can be selected from SEQ ID NO:3 or SEQ ID NO:4. The junction sequences in SEQ ID NO:5 and SEQ ID NO:6 represent 9 polynucleotides on each side of an insertion site of the transgene sequence fragment and alfalfa genomic DNA in J-163, longer or shorter polynucleotide junction sequences can be selected from SEQ ID NO:7 or SEQ ID NO:8. The junction molecules (SEQ ID NO:1, 2, 5 and 6) are useful as DNA probes or DNA primer molecules in methods for DNA detection. DNA amplicons comprising the junction molecules SEQ ID NO:1, 2, 5 or 6 are aspects of the present invention, as well as the alfalfa plants and parts thereof from which the DNA amplicons are produced in DNA amplification methods that contain alfalfa genomic DNA.

A deposit of the Monsanto Technology LLC, alfalfa seed of events J-101 and J-163 disclosed above and recited in the claims has been made under the Budapest Treaty with the American Type Culture Collection (ATCC), 10801 University Boulevard, Manassas, Va. 20110. The ATCC accession number for J-101 is PTA-4814 and for J-163 is PTA-4815. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

The invention claimed is:

1. A seed of an alfalfa plant comprising event J-163 and having representative seed comprising said event deposited with American Type Culture Collection (ATCC) with Accession No. PTA-4815.

2. An alfalfa plant or parts thereof produced by growing the seed of claim 1.

3. The alfalfa plant or parts thereof of claim 2 comprising pollen, ovule, flowers, shoots, roots, or leaves.

4. A progeny plant or parts thereof of the alfalfa plant of claim 2, wherein said progeny plant or parts thereof comprise alfalfa event J-163.

5. The progeny plant or parts thereof of claim 4 further comprising pollen, ovule, flowers, shoots, roots, or leaves.

6. The progeny plant alfalfa plant or parts thereof of claim 4, the genome of which produces a J-163 diagnostic amplicon.

7. A method of producing a plant that tolerates application of glyphosate herbicide comprising:
   (a) sexually crossing a first glyphosate tolerant alfalfa plant comprising event J-163 and a second parent plant that lacks the tolerance to glyphosate herbicide, thereby producing a plurality of first progeny plants; and
   (b) selecting a first progeny plant that is tolerant to application of glyphosate; and
   (c) selfing said first progeny plant, thereby producing a plurality of second progeny plants; and
   (d) selecting from said second progeny plants a glyphosate tolerant plant.

8. An admixture of seed of alfalfa plants comprising event J-101 and event J-163.

9. A field of plants grown from a mixture of seed of comprising event J-101 and event J-163.

10. An alfalfa plant, seed, or part thereof comprising alfalfa event J-163.

11. An alfalfa plant, seed, or part thereof capable of producing a J-163 diagnostic amplicon.

12. The alfalfa plant, seed, or part thereof of claim 11, wherein the diagnostic amplicon comprises SEQ ID NOS:5, 6, 7, or 8.

13. The alfalfa plant, seed, or part thereof of claim 10 further comprising alfalfa event J-101.

14. A method of producing essentially weed-free alfalfa hay comprising the steps:
   (a) planting a field using seed according to claim 8, 10, or 13;
   (b) applying to the resulting field of alfalfa plants one or more doses of glyphosate sufficient to kill weeds but which is tolerated by the alfalfa plants; and
   (c) harvesting one or more crops of alfalfa hay from said field.

15. An alfalfa plant, seed, or part thereof capable of producing a J-163 diagnostic amplicon and a J-101 diagnostic amplicon.

16. The alfalfa plant, seed, or part thereof of claim 15, wherein the J-163 diagnostic amplicon comprises SEQ ID NOS:5, 6, 7, or 8, and wherein the J-101 diagnostic amplicon comprises SEQ ID NOS:1, 2, 3, or 4.

17. A method of producing alfalfa seed with a glyphosate tolerant trait comprising:
   (a) crossing a glyphosate tolerant alfalfa plant comprising event J-163 with another alfalfa plant;

(b) obtaining at least one progeny plant derived from the cross of (a);
(c) selecting progeny that are glyphosate tolerant, wherein said progeny comprises event J-163;
(c) obtaining at least one seed from the progeny plant.

18. The method of claim 17, wherein said selecting step (c) is spraying with glyphosate.

19. The method of claim 17, wherein said selecting step (c) is detecting a DNA molecule selected from the group consisting of SEQ ID NO:5, SEQ ID NO:6, SEQ ID NO:7, and SEQ ID NO:8.

20. The method of claim 17, wherein said selecting step (c) is detecting the presence of a CP4-EPSPS protein.

* * * * *

UNITED STATES PATENT AND TRADEMARK OFFICE
CERTIFICATE OF CORRECTION

PATENT NO. : 8,124,848 B2  
APPLICATION NO. : 12/456291  
DATED : February 28, 2012  
INVENTOR(S) : Kim A. Beazley et al.

Page 1 of 1

It is certified that error appears in the above-identified patent and that said Letters Patent is hereby corrected as shown below:

Title Page, Item (73), please insert, --Forage Genetics, Inc., West Salem, WI--

Signed and Sealed this
Fifth Day of January, 2016

Michelle K. Lee
*Director of the United States Patent and Trademark Office*